United States Patent
Nehren et al.

(10) Patent No.: US 6,503,994 B1
(45) Date of Patent: Jan. 7, 2003

(54) SILICONE COMPOSITION CURING AT ROOM TEMPERATURE AND THE USE THEREOF

(75) Inventors: Klaus-Dieter Nehren, Dormagen (DE); Michael Freckmann, Cologne (DE); Matthias Schaub, Duesseldorf (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 0 days.

(21) Appl. No.: 09/653,445

(22) Filed: Aug. 31, 2000

(30) Foreign Application Priority Data

Sep. 6, 1999 (DE) .......................... 199 42 467

(51) Int. Cl.[7] .............................................. C08G 77/08
(52) U.S. Cl. ............................ 528/17; 528/18; 528/34; 523/109; 524/588; 524/368; 524/378; 524/377
(58) Field of Search .............................. 528/17, 18, 34; 524/588, 368, 378, 377; 523/109

(56) References Cited

U.S. PATENT DOCUMENTS

| | | | |
|---|---|---|---|
| 4,174,338 A | | 11/1979 | Goller et al. ............ 260/37 |
| 4,261,758 A | * | 4/1981 | Wright et al. .......... 106/287.12 |
| 4,537,944 A | * | 8/1985 | Imai et al. .............. 528/18 |
| 4,609,687 A | | 9/1986 | Schwabe et al. ........... 523/109 |
| 4,891,400 A | | 1/1990 | Schwabe et al. ........... 524/745 |
| 5,118,290 A | | 6/1992 | Müller et al. ............. 433/48 |
| 6,218,461 B1 | * | 4/2001 | Schwabe et al. ........... 524/588 |

FOREIGN PATENT DOCUMENTS

| | | | |
|---|---|---|---|
| DE | 1 153 169 | 8/1963 | |
| DE | 26 44 193 A1 | 4/1978 | .......... C08L/83/04 |
| DE | 34 06 233 A1 | 8/1985 | .......... C08L/83/04 |
| DE | 36 36 974 A1 | 5/1988 | .......... C08G/18/10 |
| DE | 43 32 037 A1 | 3/1995 | .......... A61K/6/10 |
| DE | 296 13 945 U1 | 1/1998 | .......... B05K/17/005 |
| EP | 0 219 660 A2 | 4/1987 | .......... C08L/83/04 |
| EP | 0 378 806 B1 | 7/1990 | .......... B05C/17/005 |
| EP | 0 939 107 | 1/1999 | |

OTHER PUBLICATIONS

Ullmann's Encyclopedia of Industrial Chemistry, 5th ed., Weinheim; New York; VCH, vol. 8, 1987, 288.

Römpp Chemie Lexikon, 9th ed., Stuttgart; New York: Georg Thieme Verlag, vol. 5, 3508.

* cited by examiner

*Primary Examiner*—Margaret G. Moore
(74) *Attorney, Agent, or Firm*—Norris McLaughlin & Marcus

(57) ABSTRACT

Among other things, a silicone composition curing by condensation at room temperature is prepared from a base dough containing filler and polyorganosiloxane having hydroxy groups, as well as from an activator component containing crosslinker and a catalyst of an organometallic compound, which is characterized in that the activator component additionally contains a polyether having at most one alkoxysilyl group and/or a polyaddition product based on polyether and having at most one alkoxysilyl group.

12 Claims, No Drawings

SILICONE COMPOSITION CURING AT ROOM TEMPERATURE AND THE USE THEREOF

The invention relates to silicone compositions which cure by condensation at room temperature, composed of polyorganosiloxane containing hydroxyl groups and base dough containing filler, as well as an activator component containing crosslinking agents and a catalyst composed of an organic metal compound.

Silicone impression compositions which crosslink by condensation and crosslink by addition differ according to the nature of the crosslinking (R. Marxkors/H. Meiners, Taschenbuch der zahnärztlichen Werkstoffkunde, Munich Vienna: Carl Hanser Verlag, 1978; Ullmann's Encyclopedia of Industrial Chemistry, 5th ed., Weinheim; New York; VCH, Volume 8, 1987, 288).

The silicone impression compositions in the form of a two-component system consist—if they belong to those that crosslink by condensation—of base dough containing polydimethylsilanols or other hydroxy polyorganosiloxanes and filler as well as an activator fluid or dough containing crosslinker and catalyst for the polycondensation. After the two components are mixed just prior to use the polydimethylsilanols react with the crosslinker—usually consisting of silicic acid esters or other alkoxysilanes—by condensation with chain lengthening, branching and crosslinking, plus rubber-elastic materials well suited to the stripping operation. Silicone impression compositions crosslinking by condensation are disclosed, for example, in DE 1 153 169 B1, DE 26 44 193 A1, DE 34 06 233 A1, DE 36 36 974 A1 and DE 43 32 037 A1.

DE 1 153 169 B 1 relates to a method for producing elastomeric molded articles from two separate dough-like compositions which are mixed together before curing at room temperature. One of the compositions contains hydroxyl end-blocked diorganopolysiloxane and crosslinkers, for example silicic acid esters or organohydropolysiloxanes, and the other by contains diorganopolysiloxane end-blocked by triorganosiloxy groups and the condensation catalyst, for example dibutyltin diacetate. The compositions are used mainly as impression or sealing compositions for technical, artistic, or especially for dental purposes. It is disadvantageous that the composition containing the hydroxyl end-blocked diorganopolysiloxane and the crosslinker loses its effect considerably while in storage.

DE 26 44 193 A1 discloses doughy compositions for polyorganosiloxanes which are vulcanizable at room temperature; in addition to crosslinking substances and catalysts, they contain as thickening agents 3–40 weight-% of active hydrophilic silicic acid and in some cases up to 40 weight-% of inactive fillers such as quartz flour or titanium dioxide as well as crosslinking substances and catalysts (hardening catalysts). Crosslinking substances are silicic and polysilicic acids, and alkylalkoxy arylalkoxy or alkylalkanoyl silanes. Their quantity amounts to 0.1–10 weight-parts with respect to the polyorganosiloxane. Catalysts are carboxylic acid metal salts, such as dibutyltin dilaurate, tin(II) octanoate, lead laurate, cobalt naphthenate and tetraisopropyltitanate, or amines or amine salts, respectively, such as hexylamine, cyclohexylamine and butylammonium acetate. They are used in amounts between 0.1 to 10% with respect to the polyorganosiloxane. The dough compositions have good shelf life in moisture-proof packaging and, like the polyorganosiloxane doughs, they can be packed in tubes with a selected opening diameter and dispensed according to the length of the strands pressed from the tubes. The diameters of the tube openings are selected such that there are between 3 and 40 weight-parts of the dough compositions per 100 weight-parts of the polyorganosiloxane doughs.

In DE 34 06 233 A1, certain finely divided inorganic fillers are described for silicone compositions in dough form which cure by condensation or addition at room temperature; their particles are coated with paraffin oil, have an average particle size between 1 and 25 micrometers, and can consist of calcium carbonate, cristobalite or quartz flour. The silicone compositions contain 30–90 weight-% of the fillers and are used preferably in impression compositions for dental purposes, a distinction being made between condensation crosslinking and addition crosslinking systems. In the former case the activator components in liquid or dough form contain a carboxylic acid metal salt and a silicic acid ester, and the silicone compositions contain polyorganosiloxanes with two or more hydroxyl groups in the molecule.

In DE 43 32 037 A1, a condensation-crosslinking silicone is proposed for making impressions in dental medicine, whose principal and secondary components are mixed together in a 1:1 ratio and can be packed in the 1:1 volume ratio in chambers of dual cartridges. The principal component consists of hydroxypolysiloxane, pyrogenic silicic acid, calcium carbonate, water, and dibutyltin dilaurate, the secondary components of cristobalite, silicone oil and paraffin oil. This silicone, however, contains no crosslinker and therefore does not cure to form a rubber-elastic material.

While in the case of addition-crosslinking impression compositions, two-component systems in the form of doughs of good shelf life, which can be dispensed by weight or volume, preferably in a 1:1 ratio, are known (see for example EP 0 219 660 B1), there are no systems among the condensation-crosslinking silicone impression compositions containing crosslinking agents and having long shelf life which can be dispensed in this manner.

The invention is therefore addressed to the problem of finding a silicone composition of the kind described above, which will cure by condensation at room temperature and consist of the two components, namely base dough and the activator component, both components being stable in storage, can be dispensed in the desired ratio of mixture to one another, and can be uniformly mixed together in any ratio. The activator component is to have a fluid to doughy consistency and is to permit the silicone composition to be offered in tubes, in tubular bags intended for use together with cartridges and disclosed for example in DE 296 02 111 U1, and preferably in dual cartridges. The silicone composition is to be suitable for use as a dental impression composition.

Dual cartridges are two-chamber devices of the kind described, for example, in EP 0 378 806 B1 for mixing components which react with one another and for dispensing the dough mixtures obtained. Before use the stopper originally sealing the dual cartridge is removed and a static mixer provided at its front end with a dispensing opening is inserted. With dual cartridges the correct ratio of admixture of the components and the uniformity of the mixed doughs are easy to achieve.

The silicone composition representing the solution of the problem is characterized according to the invention by the following variants:

1. The activator component additionally contains a polyether having no more than one alkoxysilyl group and/or contains a polyaddition product based on polyether and having no more than one alkoxysilyl group.

2. The activator component additionally contains a polyaddition product with at least two alkoxysilyl groups in the molecule, the polyaddition product contained in the active component being a polyaddition product containing an ether and a urethane and a urea and an alkoxysilyl group with a predominantly linear molecular structure, ether, urethane and urea segments bound only aliphatically or cycloaliphatically, and a mean molecular weight $M_n$ of 800–20,000, a) a polyether group content of >90–99.5 wt.-% b) a urethane group content of 0.5–10-wt.-% c) a urea group content of 0–10 wt.-% and d) groups of the form, —NR$^a$R$^b$, wherein R$^a$ and R$^b$ represent, independently of one another: H, $C_xH_{2x+1}$, phenyl or —(CH$_2$)$_n$—SiR$^1$R$^2$R$^3$, R$^1$, R$^2$, and R$^3$ representing, independently of one another, $C_1$ to $C_4$ alkyl.

3. The activator component additionally contains a polyaddition product with at least two alkoxysilyl groups in the molecule, the polyaddition product contained in the activator component being a polyaddition product containing ether or urethane or urea or alkoxysilyl groups with a predominantly linear molecular structure, ether, urethane and urea segments bound only aliphatically or cycloaliphatically, and a mean molecular weight $M_n$ of 800–20,000, a) a polyether group content of 25–99.5 wt.-%, b) a urethane group content of 0.5–10 wt.-% c) a urea group content of 0–10 wt.-% and d) groups of the form —NR$^a$R$^b$, wherein R$^a$ and R$^b$ represent, independently of one another: H, $C_xH_{2x+1}$, phenyl or —(CH$_2$)$_n$—SiR$^1$R$^2$R$^3$, R$^1$, R$^2$, R$^3$ representing, independently of one another, $C_1$–$C_4$ alkoxy or $C_1$–$C_4$ alkyl.

4. The activator component additionally contains a polyaddition product with at least two alkoxysilyl groups in the molecule, the polyaddition product contained in the activator component being a polyaddition product containing ether or urethane or urea or alkoxysilyl groups with a predominantly linear molecular structure, ether, urethane and urea segments bound only aliphatically or cycloaliphatically, and a mean molecular weight $M_n$ of 800–20,000, a) a polyether group content of 25–99.5 wt.-%, b) a aurethane group content of 0.5–10 wt.-% c) a urea group content of 0–10 wt.-% and d) groups of the form —NH$_2$, —NH—$C_xH_{2x+1}$, —NH—$C_6H_5$, —NH—(CH$_2$)$_{1-6}$—SiR$^1$R$^2$R$^3$ with R$^1$, R$^2$ and R$^3$ being $C_1$–$C_4$-alkoxy, $C_1$–$C_4$-alkyl, with at least one $C_1$–$C_4$-alkyl moiety; —N—$C_xH_{2x+1}$—$C_xH_{2x+1}$—, —N—$C_xH_{2x+1}$—$C_6H_5$, —N$C_xH_{2x+1}$—(CH$_2$)$_{1-6}$—SiR$^1$R$^2$R$^3$ with R$^1$R$^2$R$^3$ [=] $C_1$–$C_4$-alkoxy and/or $C_1C_4$-alkyl; —N—$C_6H_5$—(CH$_2$)$_{1-6}$—SiR$^1$R$^2$R$^3$ with R$^1$R$^2$R$^3$ being $C_1$–$C_4$ alkoxy and/or $C_1$–$C_4$ alkyl.

The activator component additionally contains a polyaddition product with at least two alkoxysilyl groups in the molecule, the polyaddition product being a polyaddition product containing ether, urethane, urea and alkoxysilyl groups having a predominantly linear molecule structure, ether, urethane and urea segments bound exclusively aliphatically or cycloaliphatically, and a molecular weight $M_n$ of 800–20,000, a) a polyether group content of 25–90 wt.-%, b) a urethane group content of 0.5–10 wt.-%, c) a urea group content of 0–<0.5 wt.-%, and d) groups of the formula —NR—(CH$_2$)$_{1-6}$—SiR$^1$R$_2$R$^3$, wherein R is hydrogen or —(CH$_2$)$_{1-6}$—SiR$^1$R$^2$R$^3$, R$^1$, R$^2$, R$^3$ representing, independently of one another, $C_1$–$C_4$-alkoxy, the content of the alkoxysilyl groups, —SiR$^1$R$^2$R$^3$, amounting to 1–25 wt.-%.

The term, polyaddition products, has the meaning, in the sense of the invention, of products obtained as a result of a polyaddition. Polyaddition is a polymerization reaction wherein polymers are built up by the often repeated addition of bisfunctional or polyfunctional educts or monomers (Römpp Chemie Lexikon, 9th ed., Stuttgart; New York: Georg Thieme Verlag, vol. 5, 3508).

The silicone composition of the first variant according to the invention has proven especially valuable when the polyether and/or the polyaddition product based on polyether is free of alkoxysilyl groups.

Furthermore, the silicone composition according to the invention according to the first variant has proven especially valuable when the polyethers contained in the activator component) are homopolymers, block copolymers or statistical copolymers of the structure:

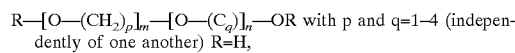

R—[O—(CH$_2$)$_p$]$_m$—[O—(C$_q$)]$_n$—OR with p and q=1–4 (independently of one another) R=H, $C_xH_{2x+1}$; x=1–100, phenyl, benzyl, benzoyl, m and n as desired, so that $M_n$=200–20,000.

Polyaddition products are disclosed, for example, in DE 36 36 974 A1. According to DE 36 36 974 A1, the polyaddition products containing ether, urethane and urea groups described therein, with alkoxysilyl groups of a predominant linear molecular structure with ether, urethane and urea segments bound exclusively (cyclo)aliphatically and with a mean molecular weight of 800–20,000 are used especially in the form of doughs for the preparation of accurate impressions of jaws with teeth, jaws with some teeth, and toothless jaws and for preparing plaster models. For this purpose, mixtures of the polyaddition products with a crosslinker, especially tetraethoxysilane, are prepared, which are then used with additional components for the preparation of impression compositions and duplicating compositions which crosslink at room temperature.

Surprisingly, by the combined use of the polyaddition products disclosed in DE 36 36 974 A1 in the activator component usually formed of crosslinker and catalytically active organometallic compound, a silicone composition consisting of a base dough and activator component is created which is characterized by the very good hydrolysis resistance and shelf life of the activator component. The consistency of the activator component can be fluid to doughy as needed. The base dough and activator component can be dispensed with accuracy both manually and automatically, and can be mixed uniformly with one another in any ratio, so that the silicone composition according to the invention can be sold advantageously also in packages which permit automatic measurement, dispensing and mixing.

For the silicone compositions according to the invention, an activator component has proven especially appropriate which contains 10–90 wt.-% of the polyaddition product and/or polyether. The amount of polyaddition product is governed by the desired consistency of the activator component, which can be fluid to doughy as required. The desired consistency depends on the form in which the silicone composition is sold to meet practical requirements.

The crosslinking agent and catalyst form the additional components of the activator. Any silicic acid esters and other alkoxysilanes known for this purpose can be used as crosslinking agents. Preferred are alkoxysilanes having 1–16 carbon atoms in the alkoxy moiety, and if desired they can also contain ethylenically unsaturated groups in the molecule, an example being vinyl trimethoxysilane.

Advantageously, the activator component contains at least one organometallic oxide and/or at least one carboxylate from the group of metals Sn, Zn, Fe, Pb, Ti, Zr and Co.

Suitable catalysts are the organic tin, titanium and zirconium compounds known in themselves for this purpose, especially dibutyl and dioctyl tin oxide and dibutyl tin dilaurate.

The concomitant use of inorganic fillers, such as silica, in the activator component is possible, but not absolutely necessary.

There is nothing special about the composition of the base dough, and it corresponds to the known silicone compositions of the condensation-crosslinking type. In addition to the polyorganosiloxane containing hydroxyl groups, the base dough furthermore contains known fillers, for example quartz, cristobalite, calcium carbonate, sodium silicate, calcium silicate and/or glass in common particle sizes and amounts, plus working adjuvants if desired, such as hydrogenated castor oil. A filler content of 5 to 50 wt.-% has proven especially valuable.

The silicone composition according to the invention is suitable for mold making, for embedding and coating and for similar applications. Using it as a dental impression composition proves especially advantageous.

For further explanation, examples of a base dough and an activator component suitable for the silicone compositions according to the invention will be described below.

EXAMPLE 1

Base Component

In a vacuum planetary mixer, the following are mixed together in the stated order at room temperature and normal pressure at 50 rpm for 30 minutes to form a dough: 74 wt.-% of polydimethylsiloxane containing hydroxyl groups, with a viscosity of 2,000 mPas at 23° C., 25 wt.-% of a mixture of inorganic fillers, and 1 wt.-% of organic dye. Then the dough was degassed in vacuo for another 5 minutes. The finished dough is then packed (a) in tubes, (b) in tubular bags, and (c) in one of the two chambers of dual cartridges.

EXAMPLE 2

Activator Component A

As described in DE 36 36 974 A1, a polyaddition product having terminal alkoxysilyl groups is synthesized from a polyether made of propylene oxide, ethylene oxide and propylene glycol (86.3 wt.-%), isophorone diisocyanate (9.6 wt.-%) and N-methylaminopropyl trimethoxysilane (4.1 wt.-%). 75 wt.-% of the polyaddition product is uniformly mixed with 25 wt.-% of a preparation obtained from vinyl trimethoxysilane and dibutyl tin oxide by refluxing for one hour at 120° C. and then cooling. The activator component thus obtained is packed (a) in tubes, (b) in tubular bags, and (c) in the second chamber of the dual cartridge whose first chamber already contains the base dough.

EXAMPLE 3

Activator Component B

By the method described in DE 36 36 974 A1 a polyaddition product containing no terminal alkoxysilyl groups is synthesized from a polyether prepared from propylene oxide, ethylene oxide and propylene glycol (87.5 wt.-%), isophorone diisocyanate (9.7 wt.-%) and hexylamine (2.8 wt.-%). 75 wt.-% of the polyaddition product is uniformly mixed together with 25 wt.-% of a preparation obtained from vinyl trimethoxysitane and dibutyl tin oxide by heating for one hour at 120° C. with refluxing and then cooling. The activator component obtained is packed in (a) tubes, (b) in tubular bags, and (c) in the second chambers of dual cartridges whose first chambers already contained the base dough.

EXAMPLE 4

Activator Component C

A polyaddition product free of urea groups is synthesized from a polyether prepared from propylene oxide, ethylene oxide and propylene glycol (89.05 wt.-%), isophorone diisocyanate (3.3 wt.-%) and isocyanatopropyl triethoxysilane (7.65 wt.-%). 75 wt.-% of the polyaddition product is mixed uniformly together with 25 wt.-% of a preparation obtained from vinyl trimethoxysilane and dibutyl tin oxide by refluxing for one hour at 120° C. and then cooling. The activator component obtained is packed (a) in tubes, (b) in tubular bags and (c) in the second chambers of dual cartridges whose first chambers already contain the base dough.

EXAMPLE 5

Activator Component D 75 wt.-% of a polytetrahydrofuran with an average molecular weight of 2,000 is heated at 60° C. and mixed uniformly together with 25 wt.-% of a preparation obtained from vinyl trimethoxysilane and dibutyltin oxide by refluxing for one hour at 120° C. and then cooling. The activator component obtained after cooling to room temperature is packed (a) in tubes, (b) in tubular bags, and (c) in the second chambers of dual cartridges whose first chamber already contained the base dough.

EXAMPLE 6

Activator Component E

As described in DE 36 36 974 A1, a polyaddition product with a content of alkoxysilyl groups of 5.96 wt.-% is synthesized from isophorone diisocyanate, aminopropyl trimethoxysilane and a polyether prepared from propylene oxide, ethylene oxide and propylene glycol. 75 wt.-% of the polyaddition product is uniformly mixed with 25 wt.-% of a preparation obtained from vinyltriethoxysilane and dioctyltin oxide by heating for 24 hours at 100° C. and then cooling. The activator component obtained is packed (a) in tubes, (b) in tubular bags, and (c) in the second chambers of dual cartridges whose first chamber already contains the base dough.

EXAMPLE 7

The activator components described in EXAMPLES 2–6 are pressed, each with the base component described in example 1, from a cartridge in a volumetric ratio of 1:4 and uniformly mixed with a static mixer. In all cases compositions were obtained which crosslinked to elastomers at room temperature.

EXAMPLE 8

In order to judge shelf life, the activator components A and C and the base components were mixed together in a volumetric ratio of 1:4 immediately after being placed in the packages, and [again] after 8 weeks of storage at 30° C. and 80% atmospheric humidity, and the total working time of the silicone compositions obtained was determined. The results show that the effectiveness of the activator components is virtually unaffected by their storage.

The time in which the crosslinking has not progressed too far and thus the mixture is still workable:

Base/Activator A:

Immediately after packing: 1'50" after 8 weeks storage (30° C./80% RH): 1'45"

Base/Activator C:

Immediately after packing: 1'55" after 8 weeks storage (30° C./80% RH): 2'05".

What is claimed is:

1. A two-component silicone composition curing by condensation at room temperature, comprising a first component further comprising a base dough containing filler and a polyorganosiloxane having hydroxyl groups, and a second component further comprising an activator component containing crosslinkers, and a catalyst of an organometallic compound, wherein the activator component additionally contains a polyaddition product based on polyether and having at most one alkoxysilyl group and/or a polyether having at most one alkoxysilyl group.

2. Silicone composition according to claim 1, wherein the polyaddition product is free of alkoxysilyl groups.

3. Silicone composition according to claim 2, characterized in that the polyethers contained in the activator component are homopolymers, block copolymers or statistical copolymers of the structure R—[O—(CH$_2$)$_p$]$_m$—[O—(C$_q$H$_{2q}$)]$_n$—OR with p and q=1–4 (independently of one another) R=H, C$_x$H$_{2x+1}$; x=1–100, phenyl, benzyl, benzoyl, m and n as desired, so that M$_n$=200–20,000.

4. Silicone composition according to claim 1, wherein the amount of polyaddition product and/or polyether in the activator component amounts to 10–90 wt.-%.

5. Silicone composition according to claim 4, characterized in that the amount of polyaddition product in the activator component amounts to 30–60 wt.-%.

6. Silicone composition according to claim 1 wherein the activator component contains at least one organometallic oxide and/or at least one carboxylate salt having a metal selected from the group consisting of Sn, Zn, Fe, Pb, Ti, Zr and Co.

7. Silicone composition according to claim 1, wherein the activator component contains dibutyl or dioctyltin oxide.

8. Silicone composition according to claim 1 wherein the base dough has a filler content of 5–80 wt.-%.

9. Silicone composition according to claim 1 wherein the packaging of base dough and activator component are packaged in tubes.

10. Silicone composition according to claim 1 wherein the base dough and activator component are packaged in tubular bags.

11. Silicone composition according to claim 1, wherein the base dough and activator component are packaged in dual cartridges.

12. A dental impression composition comprising the silicone composition of claim 1.

* * * * *